United States Patent
Atzinger

(10) Patent No.: US 6,872,000 B2
(45) Date of Patent: Mar. 29, 2005

(54) X-RAY APPARATUS

(75) Inventor: Franz Atzinger, Nuremberg (DE)

(73) Assignee: Siemens Aktiengesellschaft, Münich (DE)

( * ) Notice: Subject to any disclaimer, the term of this patent is extended or adjusted under 35 U.S.C. 154(b) by 167 days.

(21) Appl. No.: 10/316,690

(22) Filed: Dec. 11, 2002

(65) Prior Publication Data

US 2003/0112926 A1 Jun. 19, 2003

(30) Foreign Application Priority Data

Dec. 13, 2001 (DE) .......................................... 101 61 322

(51) Int. Cl.⁷ .............................................. H05G 1/02
(52) U.S. Cl. ..................................................... 378/197
(58) Field of Search ................................. 378/195–198

(56) References Cited

U.S. PATENT DOCUMENTS

| | | | | |
|---|---|---|---|---|
| 4,412,346 A | * | 10/1983 | Takenouti et al. ........... | 378/181 |
| 4,435,830 A | * | 3/1984 | Suzuki et al. ............... | 378/197 |
| 4,541,293 A | * | 9/1985 | Caugant et al. ............. | 74/89.18 |
| 5,038,371 A | | 8/1991 | Janssen et al. | |
| 5,050,204 A | * | 9/1991 | Siczek et al. ............... | 378/197 |
| 5,291,540 A | | 3/1994 | Futamata | |
| 5,515,416 A | * | 5/1996 | Siczek et al. ............... | 378/197 |
| 6,155,713 A | * | 12/2000 | Watanabe ................... | 378/197 |
| 6,554,472 B1 | * | 4/2003 | Dietz et al. ................. | 378/197 |
| 6,733,176 B2 | * | 5/2004 | Schmitt ...................... | 378/196 |

FOREIGN PATENT DOCUMENTS

DE  8710117.3  12/1988

* cited by examiner

Primary Examiner—Craig E. Church
Assistant Examiner—Thomas R. Artman
(74) Attorney, Agent, or Firm—Schiff Hardin LLP

(57) ABSTRACT

An X-ray apparatus has a radiation source and a radiation receiver that are movably mounted at a stand arranged at the ceiling of an installation room. The stand has a first slide system and a second slide system with respective slide directions that are orthogonal relative to one another. A rotary device that is displaceable via the second slide system is provided at the second slide system. The radiation source and the radiation receiver are seated so as to be rotatable in common via the rotary device. The radiation source and the radiation receiver are arranged at respective telescoping carriers that are in turn displaceable at a third slide system that is arranged at the rotary device and that is rotatable by the rotary device.

4 Claims, 2 Drawing Sheets

X-RAY APPARATUS

BACKGROUND OF THE INVENTION

1. Field of the Invention

The present invention is directed to an X-ray apparatus of the type having a radiation source and a radiation receiver that are movably seated via a stand arranged at the ceiling of an installation room, the stand having a first slide system and a second slide system that respectively slide along slide directions that are orthogonal relative to one another, and wherein a rotary device that is displaceable via the second slide system is provided at the second slide system, the radiation source and the radiation receiver being mounted so as to be rotatable in common via the rotary device.

2. Description of the Prior Art

Such X-ray apparatuses having a stand arranged at the ceiling that enables movement of the X-ray source and the X-ray receiver, for example a solid-state detector, in the x-direction and in the y-direction are known and make it possible for the examining person to arrange the radiation source and the radiation receiver in a multitude of positions relative to one another. In order to register the required exposures of an examination subject, for example a patient, that is arranged on a central patient support table. This arrangement, however, has the disadvantage that some standard projections as are required for the implementation of X-ray exposures are not possible on the basis of the x-y support. Such projections are projections that must be implemented from the front the left and the right (as seen from the point of view of the patient) for patients having a fixed position. Known systems of this type allow only one projection in one direction since the positioning of the radiation source and the radiation receiver is fixed with respect to the respective sides of the table. When a projection is to be registered from the opposite direction, then it is necessary that the system be repositioned and the patient must be removed from and then again placed on the patient support.

U.S. Pat. No. 5,050,204 discloses an X-ray apparatus of this type wherein a parallelogram mount is arranged at a turntable at the ceiling, with a C-arm at one end of the parallelogram mount, to which the radiation source and the radiation receiver are attached. The slide mechanism at the ceiling is positioned such that it is not above the patient; the lateral offset is compensated via the parallelogram mechanism.

U.S. Pat. No. 5,038,371 likewise discloses a C-arm X-ray apparatus wherein the radiation source and the radiation receiver are arranged at the ends of a C-arm that is displaceably accepted in a base that is rotatable around a horizontal axis. The radiation receiver is seated somewhat displaceable relative to the radiation source.

Further, U.S. Pat. No. 5,291,540 likewise discloses a C-arm X-ray apparatus, and German Utility Model 87 10 117 discloses a ceiling stand for an X-ray examination apparatus having a telescoping column.

SUMMARY OF THE INVENTION

An object of the present invention is to provide an X-ray apparatus that offers the examining person more positioning possibilities than conventional systems.

This object is inventively achieved in an X-ray apparatus of the type initially described wherein the radiation source and the radiation receiver are arranged at telescoping carriers that are in turn displaceable at a third slide system that is arranged at the rotary device and that is rotatable via the rotary device.

The use of the inventive rotary device makes it possible to turn the radiation source and the radiation receiver in common around a vertical rotational axis, so that their positioning with respect to the respective table side can be completely changed by means of a 180° rotation. The rotary device, which is expediently fashioned as a rotary table, preferably is arranged at the second slide system, i.e. it is itself displaceably seated, and the vertical rotational axis likewise can be displaced. Due to the x-y mobility and the rotational possibility that are established this by arrangement, the physician can target positions, and thus register projections, that would not be possible with known systems.

In an embodiment the third slide system that is rotatable via the rotary device and at which the radiation source and the radiation receiver are displaceably arranged is arranged at the rotary device, particularly the rotatable table. A further adjustment thus is achieved possibility that, in particular, enables the setting of the film-to-focus distance, i.e. the spacing of the radiation source from the radiation receiver.

In order also to enable an adaptation of the vertical position of the radiation source and of the radiation receiver, in an embodiment the radiation source and the radiation receiver are arranged at telescoping carriers that are in turn arranged at the rotary device, or at the third slide system. As a consequence, it is possible for the radiation source and the radiation receiver to be flexibly positioned in height.

In order also to be able to register vertical projections, preferably the radiation source and the radiation receiver are rotatably arranged at respective carriers, i.e. they are respectively rotatable around different horizontal axes. Additionally, it is expedient when they are additionally rotatable around a vertical carrier axis.

DESCRIPTION OF THE PREFERRED EMBODIMENTS

Figure 1:
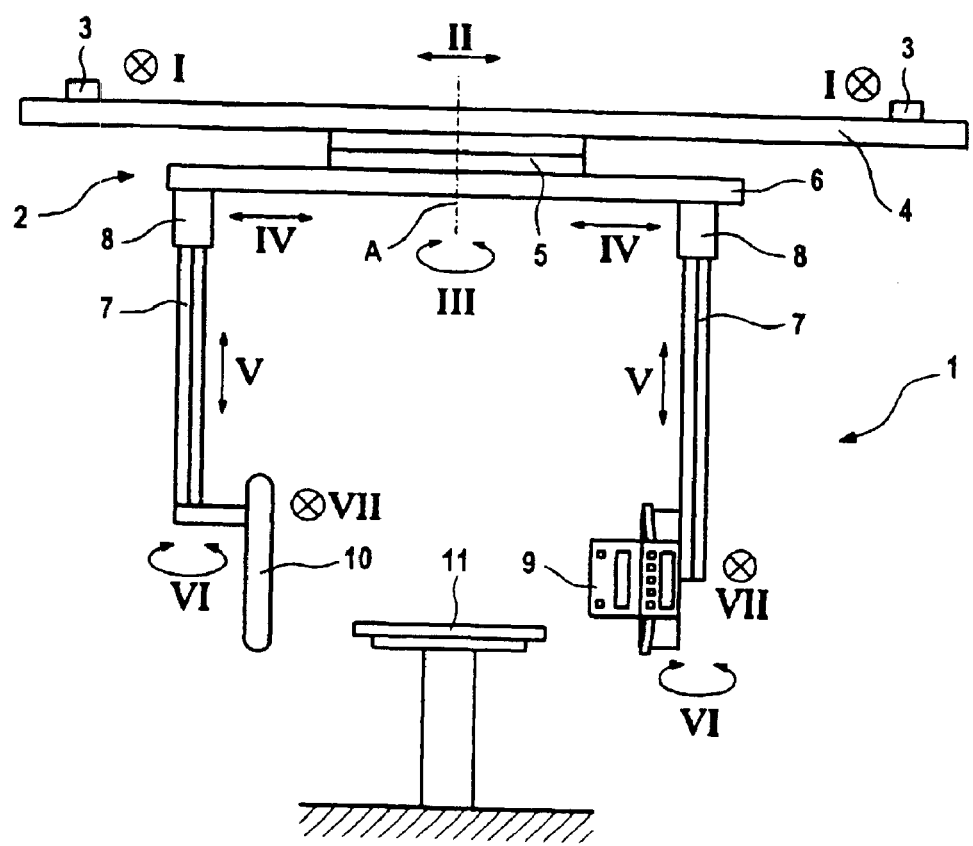
FIG. 1 is a schematic illustration of an inventive X-ray apparatus in a first positioning attitude.

FIG. 1 shows an inventive X-ray apparatus 1 having a stand 2 arranged at the ceiling of an installation room that has a first slide system composed, for example, of two slide rails. A second slide system 4 that is arranged at suitable carriages (not shown in detail) that are displaceable on the rails of the slide system 3 is displaceably seated at this slide system 3. A rotary device 5 in the form of a rotatable table having a vertical rotational axis A is also arranged—likewise via a carriage (not shown) or the like—at the slide system 4, which likewise has a suitable rail or the like. A third slide system 6 is arranged at the rotary device 5. The third slide system 6 also has a rail or the like at which two telescoping carriers 7 are displaceably held via sliding carriages 8. A radiation source 9 and a radiation receiver 10, for example a solid-state image detector, are arranged at the telescoping carriers 7, respectively.

The design shown in FIG. 1 allows a versatile displacement of the radiation source 9 and of the radiation receiver 10. For example, the second slide system 4 is displaceable in x-direction (which proceeds into the plane of the drawing here, as indicated by the symbol ⓧ I) at the first slide system 3 secured to the ceiling side. The rotary device 5 is in turn displaceable in y-direction (as indicated by the double arrow II) at the second slide system 4, i.e. the vertical rotational axis A can be displaced in this longitudinal direction. This rotary device 5 enables a rotation of the components secured to it around the axis A, as indicated by the double arrow III. Finally, the two carriages 8 and, together with them, the telescoping arms 7 plus components arranged thereat are displaceable at the third slide system 6 in the indicated slide direction of the latter, which proceeds parallel to that of the second slide system here. This displacement possibility is indicated with the arrows IV. The telescoping nature of the two carriers 7 allows a vertical adjustment of the carrier length, as indicated by the arrows V. The radiation source 9 and the radiation receiver 10 are in turn rotatable around the vertical axis formed by the carriers 7, as indicated by the two double arrows VI. Finally, both the radiation source 9 as well as the radiation receiver 10 are rotatable around a horizontal axis, which also proceeds into the plane of the drawing here and is indicated by the symbol ⊗ VII.

As a result of this versatile adjustment possibility, it is possible to arrange the radiation source 9 and the radiation receiver 10 in approximately any arbitrary position at the side and above or below the patient support table 11. The employment of the rotary device in the form of the rotary table opens up the possibility—as seen from the viewpoint of the patient—of implementing projections from the left and right in that all components secured to the rotary table, i.e. principally the two carriers 7 plus radiation source 9 and radiation receiver 10, are turned by 180°. At the same time, the displaceable bearing of the carriers 7 via the carriages 8 at the third slide system 6 offers the possibility of being able to adjust the film-to-focus distance, i.e. the spacing between radiation source 9 and radiation receiver 10, within wide ranges, i.e. the distance between these two elements can be varied to the full extent allowed by the third system. The central ray Z can also be adjusted in this way.

Figure 2:
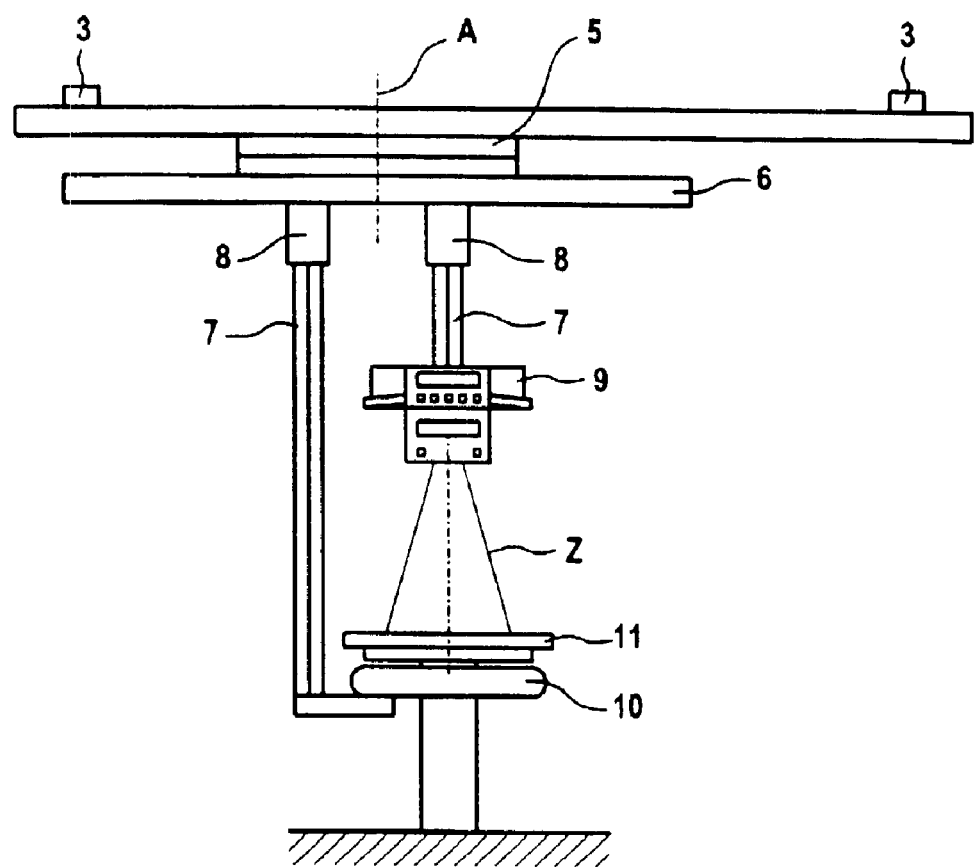
FIG. 2 shows the X-ray apparatus of FIG. 1 in a second positioning attitude.

FIG. 2 shows a second positioning possibility of the radiation source 9 relative to the radiation receiver 10. Therein, the rotary device 5 and, together with it, the rotational axis A were displaced somewhat to the left on the second slide system 4; simultaneously, the two carriages 8 and, together with them, the carriers 7 were shifted into the middle of the third slide system, namely such that the radiation source 9 is arranged directly above and the radiation receiver 10 is arranged directly under the patient support table 11. The radiation source 9 was in turn turned around the rotational axis referenced VII in FIG. 1, so that it radiates downwardly, whereas the radiation receiver 10 was also pivoted around the rotational axis VII in a corresponding way.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray apparatus comprising:
   an X-ray radiation source;
   an X-ray radiation receiver for receiving X-rays from said radiation source;
   a supporting stand having a first slide system, a second slide system and a rotary device, said first slide system being adapted for mounting to a ceiling and allowing sliding of said stand in a first slide direction, said second slide system allowing sliding of said stand in a second slide direction orthogonal to said first slide direction, and said rotary device being mounted to said second slide system for displacement by said second slide system;
   a third slide system mounted to said rotary device and being rotatable by said rotary device and displaceable relative to said rotary device; and
   a first telescoping carrier attached to said third slide system to which said radiation source is mounted, and a second telescoping carrier attached to said third slide system to which said radiation receiver is mounted, said radiation source and said radiation receiver being rotatable in common by said rotary device and being individually displaceable relative to each other by said third slide system.

2. An X-ray apparatus as claimed in claim 1 wherein said rotary device is a rotatable table.

3. An X-ray apparatus as claimed in claim 1 wherein said radiation source is rotatably mounted to said first telescoping carrier and wherein said radiation receiver is rotatably mounted to said second telescoping carrier.

4. An X-ray apparatus as claimed in claim 3 wherein said radiation source is mounted to said first telescoping carrier for rotation around a horizontal axis and around a vertical axis and wherein said radiation receiver is mounted to said second telescoping carrier for rotation around a horizontal axis and around a vertical axis.

* * * * *